United States Patent [19]

Plyley

[11] Patent Number: 5,458,279
[45] Date of Patent: Oct. 17, 1995

[54] SURGICAL STAPLER WITH SAFETY FEATURE

[75] Inventor: Alan K. Plyley, Santa Barbara, Calif.

[73] Assignee: Minnesota Mining and Manufacturing Company, St. Paul, Minn.

[21] Appl. No.: 270,110

[22] Filed: Jul. 1, 1994

Related U.S. Application Data

[63] Continuation of Ser. No. 946,039, Sep. 15, 1992, abandoned, which is a continuation of Ser. No. 699,719, May 14, 1991, abandoned.

[51] Int. Cl.$^6$ .................................................. A61B 17/068
[52] U.S. Cl. ............................. 227/176; 227/8; 227/178; 227/19
[58] Field of Search .................... 227/8, 19, 121, 227/175, 176, 177, 178, 179, 180

[56] References Cited

U.S. PATENT DOCUMENTS

| | | | |
|---|---|---|---|
| 3,494,533 | 2/1970 | Green et al. | 227/19 |
| 3,692,224 | 9/1972 | Astafiev et al. | |
| 3,844,289 | 10/1974 | Noiles. | |
| 4,086,926 | 5/1978 | Green et al. | 128/334 R |
| 4,202,480 | 5/1980 | Annett. | |
| 4,256,251 | 3/1981 | Moshofsky. | |
| 4,257,724 | 7/1985 | Chow et al. | 227/8 |
| 4,354,628 | 10/1982 | Green | 227/19 |
| 4,373,077 | 9/1984 | Noiles et al. | |
| 4,391,401 | 7/1983 | Moshofsky. | |
| 4,519,532 | 5/1985 | Foslien. | |
| 4,569,346 | 2/1986 | Poirier. | |
| 4,576,167 | 3/1986 | Noiles. | |
| 4,585,153 | 4/1986 | Failla et al. | |
| 4,591,085 | 5/1986 | Di Giovanni. | |

(List continued on next page.)

FOREIGN PATENT DOCUMENTS

| | | |
|---|---|---|
| 54764/86 | 9/1986 | Australia. |
| 54765 | 9/1986 | Australia. |
| 0373762 | 7/1988 | European Pat. Off.. |
| 0489436A1 | 6/1992 | European Pat. Off.. |
| 2744824 | 2/1980 | Germany. |
| 8302247 | 7/1983 | WIPO ................................ 227/19 |

OTHER PUBLICATIONS

"Disposable EEA Surgical Stapler and Curved Disposable EEA Surgical Stapler" Information Booklet, printed Jan. 1985.

Flickinger et al. Surgical Stapling *Gastric and Small Bowel Procedures* pp. 1–145.

Anderson et al. Surgical Stapling *Thoraci, Vascular and Esophageal Procedure* pp. 1–101.

Brolin et al. Surgical Stapling *Bariatric Procedures for Morbid Obesity* pp,. 1–115.

*Primary Examiner*—Richard K. Seidel
*Assistant Examiner*—Allan M. Schrock
*Attorney, Agent, or Firm*—Gary L. Griswold; Walter N. Kirn; Jeffrey J. Hohenshell

[57] ABSTRACT

The present invention comprises a surgical stapler including an anvil elongate in a longitudinal direction having anvil surfaces in a plane generally perpendicular to the longitudinal direction and surfaces defining an alignment aperture opening onto the anvil surfaces. A cartridge assembly is present that is movable relative to the anvil between an open position with the cartridge assembly spaced from the anvil surfaces and a closed position with the cartridge assembly and the anvil surfaces in closely spaced relationship. There is also present a longitudinally extending alignment pin mounted on the stapler for movement between an alignment position with the alignment pin extending into the alignment aperture, and a release position with the alignment pin spaced from the alignment aperture, and a mechanism which is adapted to engage the cartridge assembly for continuously preventing the cartridge assembly from moving from the open to the closed position whenever the alignment pin is in a position other than the alignment position, and for preventing the alignment pin from moving from the alignment position toward the release position when the cartridge assembly is in the closed position.

11 Claims, 7 Drawing Sheets

U.S. PATENT DOCUMENTS

| | | | |
|---|---|---|---|
| 4,605,004 | 8/1986 | Di Giovanni et al. . | |
| 4,606,344 | 8/1986 | Di Giovanni . | |
| 4,606,345 | 8/1986 | Dorband et al. . | |
| 4,607,636 | 8/1986 | Kula et al. . | |
| 4,608,981 | 9/1986 | Rothfuss et al. . | |
| 4,633,874 | 1/1987 | Chow et al. . | |
| 4,646,745 | 3/1987 | Noiles . | |
| 4,664,305 | 5/1987 | Blake, III et al. . | |
| 4,714,187 | 12/1987 | Green | 227/19 |
| 4,715,520 | 12/1987 | Roehr, Jr. et al. . | |
| 4,718,020 | 3/1988 | Green et al. | 227/19 |
| 4,741,336 | 5/1988 | Failla et al. . | |
| 4,803,088 | 9/1989 | Redmond et al. | 227/19 |
| 4,892,244 | 1/1990 | Fox et al. | 227/8 |
| 4,938,408 | 7/1990 | Bedi et al. | 227/8 |
| 4,941,623 | 7/1990 | Pruitt | 227/19 |
| 4,955,959 | 9/1990 | Tompkins et al. | 227/178 |
| 5,031,814 | 7/1991 | Tompkins et al. . | |
| 5,071,052 | 12/1991 | Rodak et al. | 227/178 |
| 5,137,198 | 8/1992 | Nobis et al. | 227/19 |
| 5,219,111 | 6/1993 | Bilotti et al. | 227/175 |

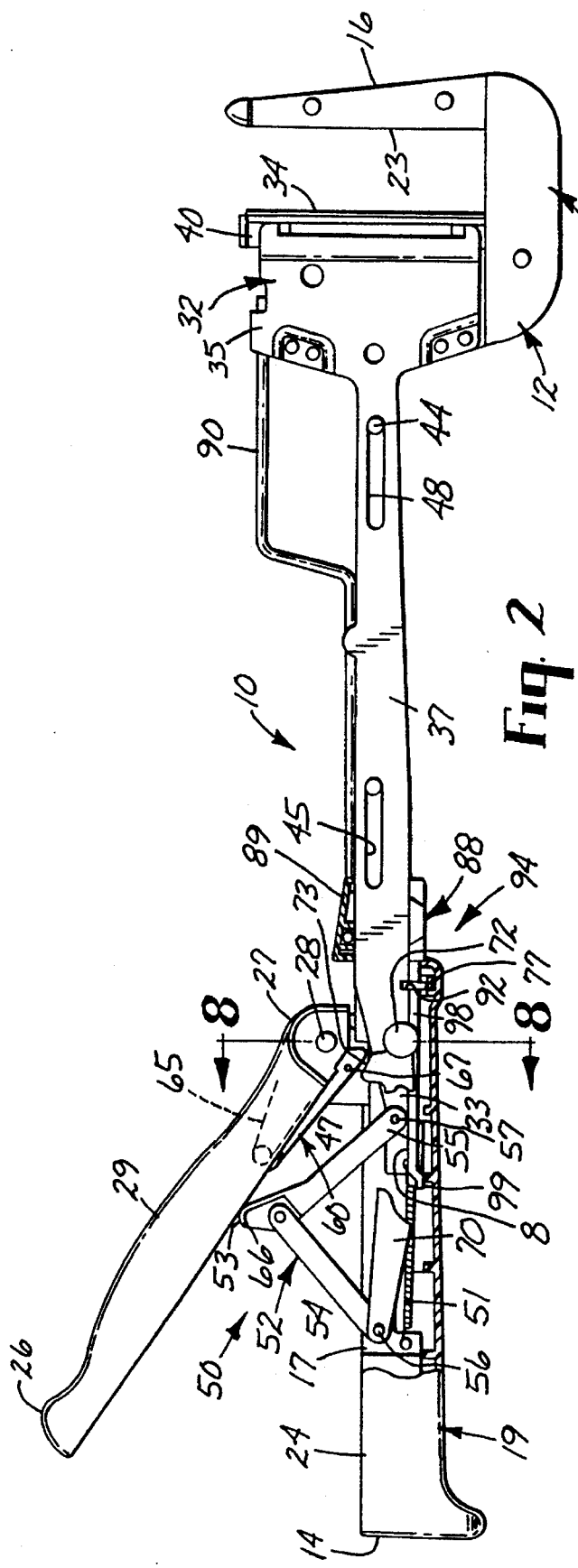

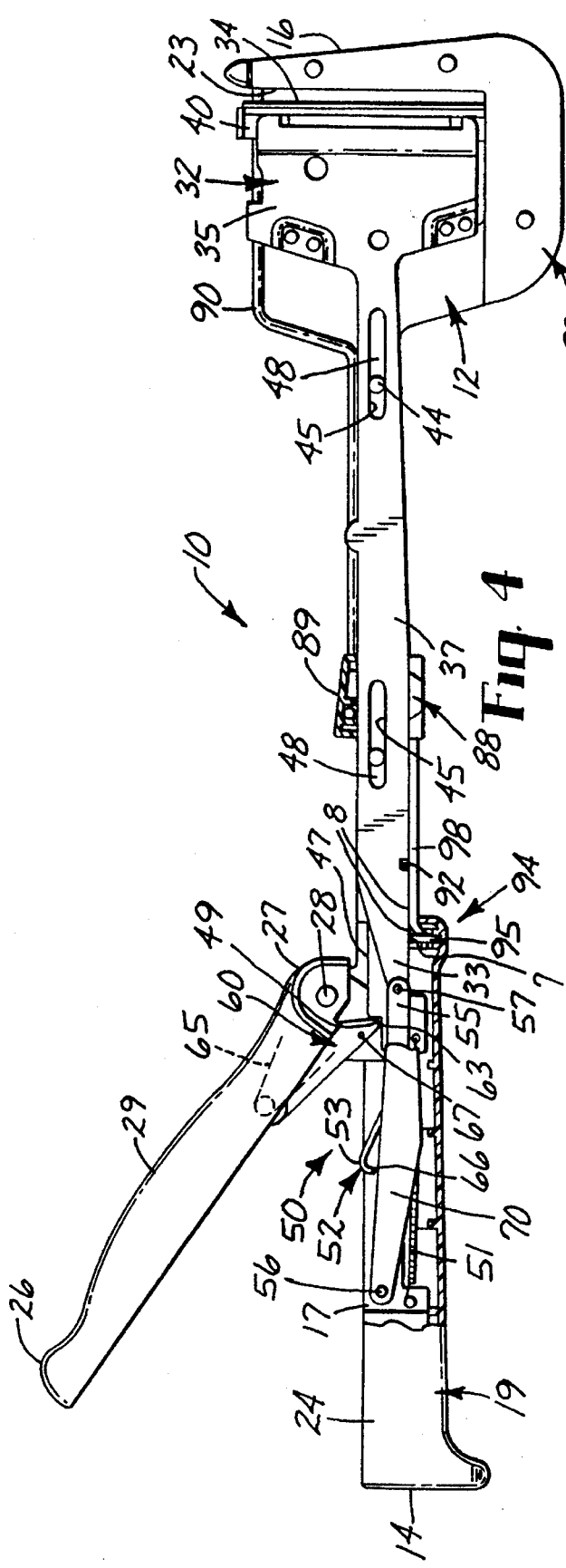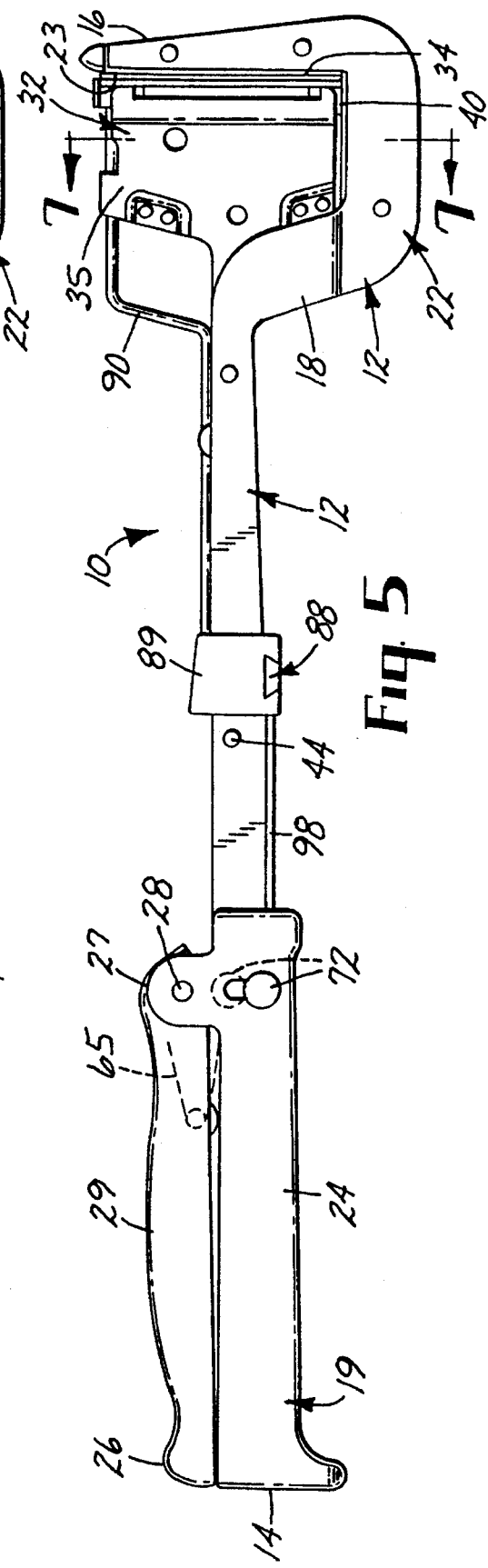

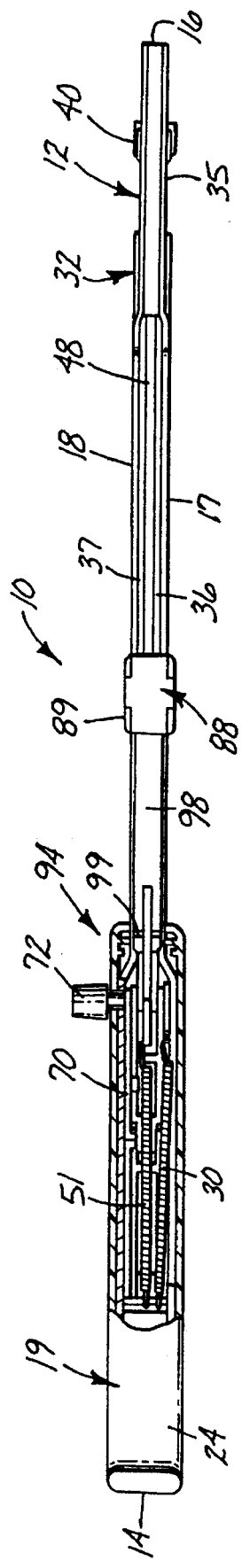
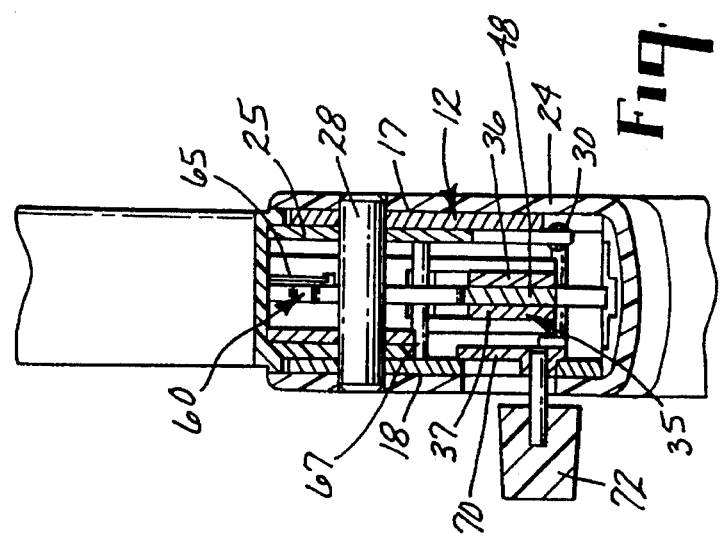
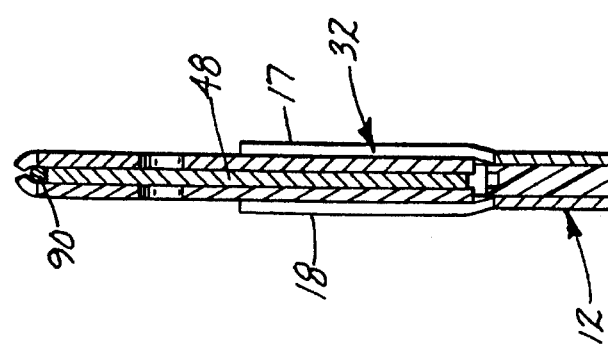
Fig. 6
Fig. 8
Fig. 7

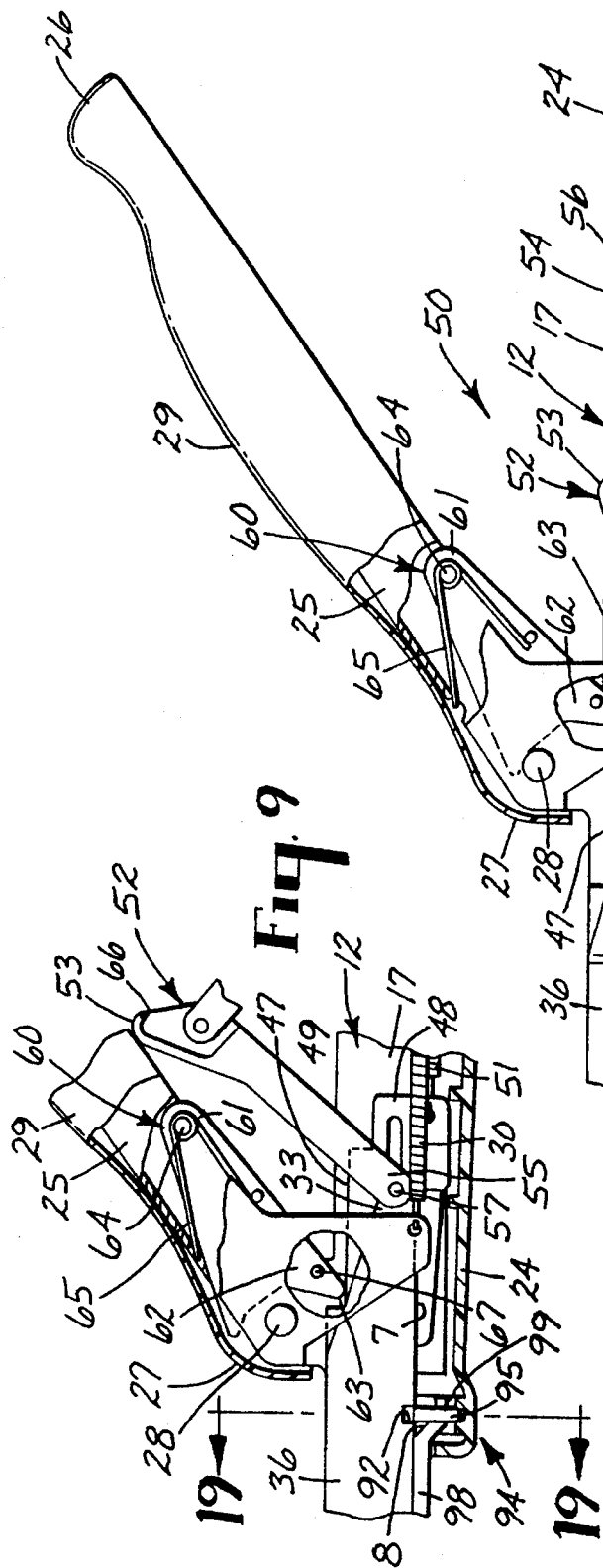
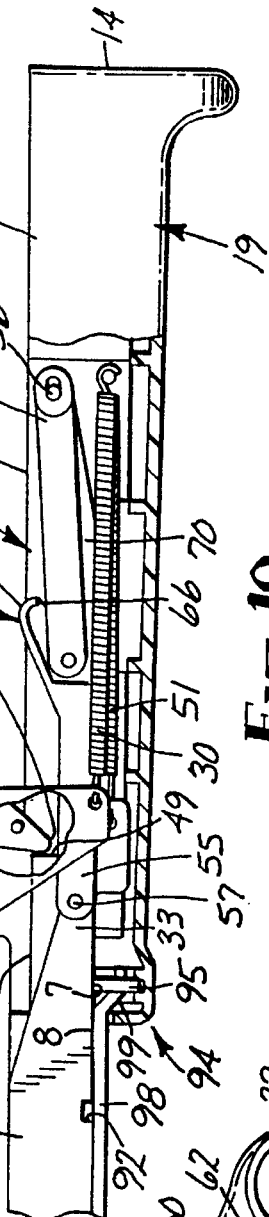
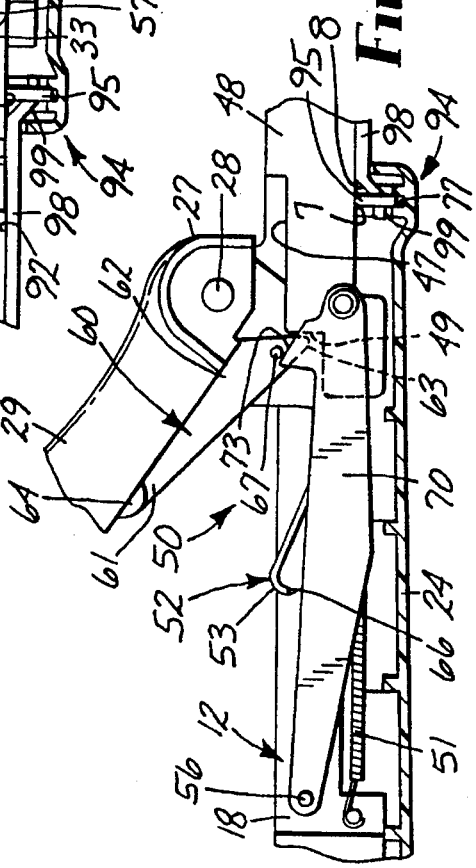
Fig. 9
Fig. 10
Fig. 11

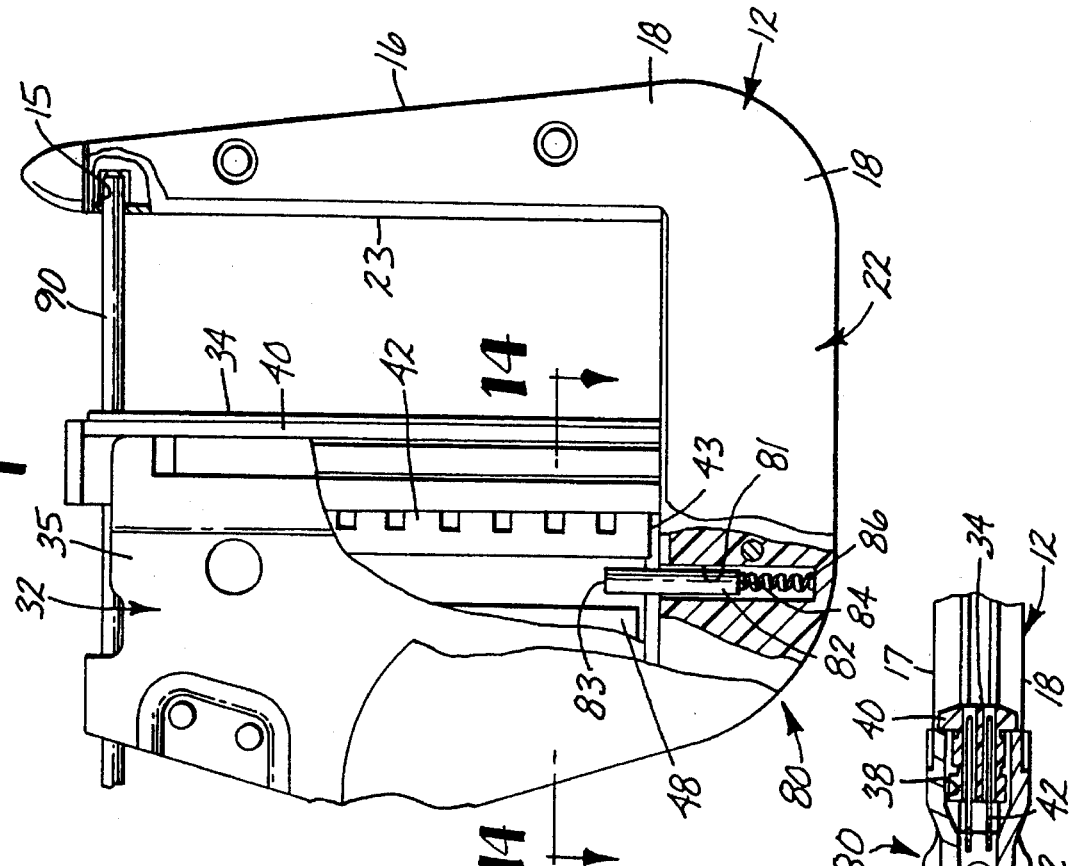
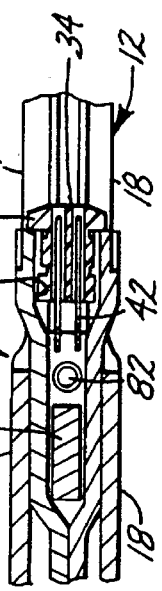
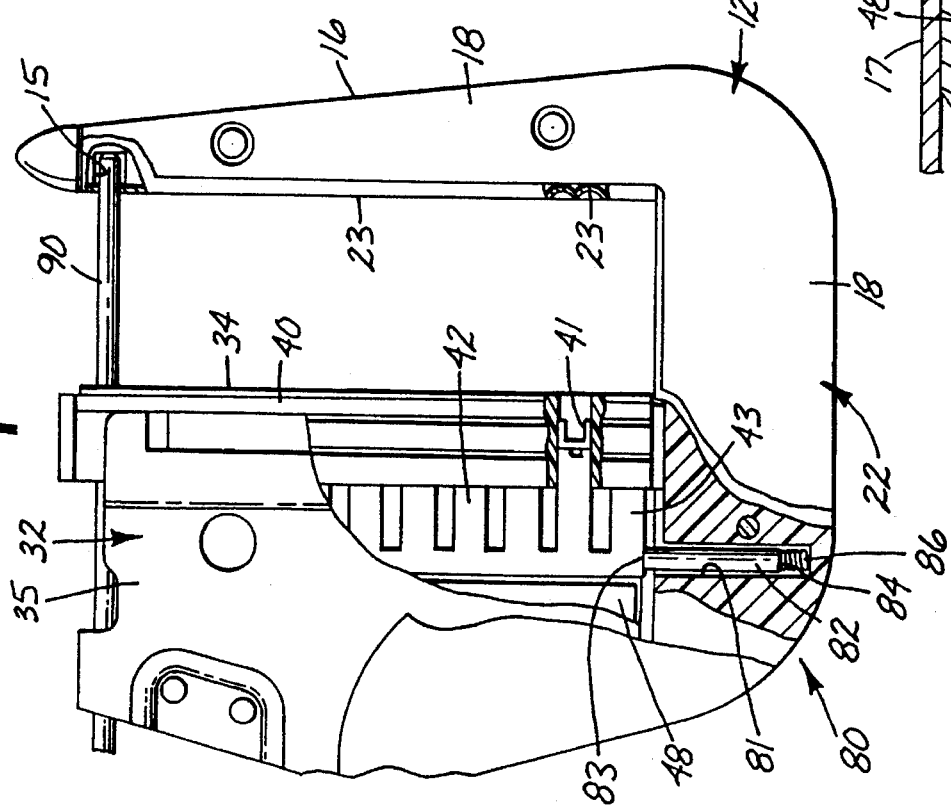

SURGICAL STAPLER WITH SAFETY FEATURE

This application is a continuation of U.S. patent application Ser. No. 07/946,039, filed Sep. 15, 1992, now abandoned, which was a continuation of U.S. patent application Ser. No. 07/699,719, filed May 14, 1991 now abandoned.

TECHNICAL FIELD

The present invention relates generally to surgical stapling instruments and particularly to the type of surgical stapling instruments used for applying linear parallel rows of staggered staples through compressed living tissue.

BACKGROUND ART

Surgical stapling instruments used for applying parallel rows of staples through compressed living tissue are well known in the art, and are commonly used, for example, for closure of tissue or organs prior to transection, prior to resection, or in anastomoses, and for occlusion of organs in thoracic and abdominal plasty procedures.

One known pneumo-intestinal surgical stapling instrument of this type has been in use for many years, and is currently available under the trade designation "The PI Stapler", catalog #3960 by Minnesota Mining and Manufacturing Company (3M), St. Paul, Minn., the use of which stapler is described in a publication entitled "Surgical Stapling, Gastric and Small Bowel Procedures, Volume I" ISBN 0-937433-00-4, Library of Congress Catalog Number 85-082599 available from Minnesota Mining and Manufacturing Company (3M), St. Paul, Minn., the contents of which are herein incorporated by reference. That stapler and a similar stapler described in Freund et al. PCT Application No. WO 83/02247, published July 7, 1983 are adapted for firing staples into compressed living tissue from a staple filled cartridge or housing.

"PI" type staplers have a handle lever, a generally C-shaped anvil portion having free and supported ends with an alignment aperture generally adjacent its free end, a cartridge transport member adapted to releasably receive a cartridge or staple housing having an alignment through passage, and an alignment pin movable between an engaged or alignment position with the alignment pin extending through the through passage in the staple housing and into the alignment aperture in the anvil jaw and a release or disengaged position with the alignment pin spaced from the alignment through passage and alignment aperture to afford removal and replacement of a spent staple cartridge.

The anvil and cartridge transport members are each elongate in a longitudinal direction, and the anvil portion has specially shaped anvil surfaces situated in a plane generally perpendicular to the longitudinal direction. When the alignment pin extends through the through passage in the staple housing and into the alignment aperture in the anvil jaw (i.e. when the alignment pin is in the alignment position), the specially shaped anvil surfaces are positioned generally opposite longitudinal slots in the cartridge or staple housing which contain unfired staples. The cartridge transport member/cartridge housing is movable between a closed or clamping position with the cartridge housing and the anvil surfaces in closely spaced relationship, and an open position with the cartridge housing and the anvil surfaces spaced farther from each other than in the closed position.

Typically, a "PI" type stapler is positioned adjacent the tissue to be stapled, the anvil and cartridge housing are approximated adjacent the tissue to be stapled, the alignment pin is moved to the alignment position, and the stapler is clamped on the tissue by moving the handle lever in a first movement to cause the cartridge holder to move toward the anvil placing the cartridge housing in the closed "clamping" position. Moving the handle lever in a second movement causes the stapler to be "fired" or causes the staples to be ejected from the cartridge.

In some surgical procedures the clamping force results in tissue that is highly compressed to ensure, inter alia, proper hemostasis in the tissues being stapled. Under a great clamping force, a prior art "PI" type stapler without an engaged alignment pin typically "scissors" or fails by deflection of the anvil portion and the cartridge housing laterally relative to one another (e.g. where the the anvil portion deflects laterally with respect to the longitudinal axis of the stapler and/or where the cartridge housing deflects in a lateral direction opposite the deflection direction of the anvil portion).

Moving the alignment pin to the alignment position before firing the stapler or before clamping tissue between the anvil and cartridge housing affords a more precisely controlled formation of the fired staples by aligning the specially shaped surfaces on the anvil portions with the staples in the cartridge housing and by preventing the cartridge housing and the specially shaped anvil surfaces from "scissoring". Moving the alignment pin to the alignment position also prevents tissue from escaping from between the anvil and cartridge housing when the cartridge assembly is clamped on the tissue to be stapled.

The prior art "PI" type staplers encounter problems because it is possible to fire the stapler or clamp tissue between the anvil and cartridge housing without the alignment pin in the alignment position. It is believed that it is difficult to determine whether the alignment pins of the prior art "PI" type staplers are engaged, particularly in the surgical environment. Also, it is possible to inadvertently fail to move the alignment pin to the alignment position. If the alignment pin is not moved to the alignment position before clamping tissue between the anvil and cartridge housing, tissue intended to be stapled may escape from between the anvil and cartridge housing resulting in incomplete anastomoses and other undesirable results. Additionally, if the alignment pin is not moved to the alignment position before the stapler is fired, the staples may be improperly formed.

Chow et al. U.S. Pat. No. 4,527,724 and assigned to Senmed, Inc., of Cincinnati, Ohio discloses a surgical stapler similar to the surgical stapler sold by Ethicon, Inc., of Somerville, N.J. under the trade name "Proximate". That stapler includes a lockout device which precludes rotation of an adjustment knob to clamp the stapler on tissue unless the alignment and retaining pin is shifted to its operative position. The lockout device, however, is only operative until the user slides the alignment and retaining pin to the operative position. Once the user slides the alignment and retaining pin to the operative position, the lockout device is not designed to be easily reactivated. Thus, to defeat the lockout device, a user need only slide the pin to the operative position and then away from the operative position. The stapler has no feature which retains the pin in the operative position when the stapler is clamped on tissue.

DISCLOSURE OF THE INVENTION

The present invention provides a surgical stapler comprising an anvil frame elongate in a longitudinal direction, anvil surfaces in a plane generally perpendicular to the longitudinal direction, surfaces defining an alignment aperture opening onto the anvil surfaces, and a cartridge assembly movable relative to the anvil frame between an open position with the cartridge assembly spaced from the anvil surfaces and a closed position with the cartridge assembly and the anvil surfaces in closely spaced relationship. The cartridge assembly comprises a cartridge housing containing a plurality of staples disposed in rows positioned in opposition to the anvil surfaces. The surgical stapler also includes a longitudinally extending alignment pin mounted on the stapler for movement between an alignment position with the alignment pin extending into the alignment aperture, and a release position with the alignment pin spaced from the alignment aperture.

By including a mechanism for engaging the cartridge assembly and anvil for continuously preventing the cartridge assembly from moving from the open to the closed position whenever the alignment pin is in a position other than the alignment position, and for preventing the alignment pin from moving from the alignment position toward the release position when the cartridge assembly is in the closed position, the present invention provides a stapler which (1) contributes to the proper formation of staples, (2) promotes proper hemostasis in the tissue to be stapled, (3) prevents "scissoring" of the anvil and cartridge portions of the stapler, (4) prevents tissue from escaping from between the anvil and cartridge housing when the cartridge assembly is clamped on the tissue to be stapled, and (5) reduces the likelihood of a weak joint or an absence of blood flow in the joint and tissue.

According to a preferred embodiment of the stapler of the present invention, there is provided a stapling instrument comprising an anvil frame having proximal and distal ends and a pair of lateral side portions that are each elongate in a longitudinal direction and spaced to define a channel therebetween. The anvil frame has a handle portion generally adjacent the proximal end with first and second ends, and a jaw portion having anvil surfaces generally adjacent the distal end. The jaw portion includes surfaces defining an alignment aperture opening onto the anvil surfaces, and the anvil surfaces are positioned in a plane generally perpendicular to the longitudinal direction.

An elongate manually movable handle or lever part having first and second ends is pivotally mounted at its second end to afford pivotal movement of the lever part relative to the anvil frame between a release position with the first end of the lever part spaced from the first end of the handle portion and an actuation position with the lever part and the handle portion in closely spaced relationship. A biasing means biases the lever part toward the release position. Preferably the biasing means comprises a coil spring mounted at one end to the anvil frame and at the other end to the lever part.

A cartridge assembly having proximal and distal ends is mounted in the channel between the lateral side portions for longitudinal movement relative to the anvil frame. The cartridge assembly comprises a cartridge transporting member having first and second side portions that are each elongate in the longitudinal direction and that are spaced to define a ram channel therebetween. The first and second side portions have surfaces defining a cartridge groove generally adjacent the distal end of the cartridge assembly. The cartridge groove surfaces are adapted to releasably receive a cartridge housing containing a plurality of staples disposed in rows positioned in opposition to the anvil surfaces, and means, such as a pusher, for pressing the staples within the cartridge housing against the anvil surfaces to engage and close the staples in tissue between the cartridge housing and the anvil surfaces. The pusher has a pair of edges and is positioned proximate the staples for movement between pre-fired and fired positions with the pusher adapted to move distally relative to the cartridge housing when the stapler is fired. The cartridge housing also includes surfaces defining an alignment through passage positioned in opposition to the alignment aperture and whose function will be described later.

A means mounts the cartridge assembly for longitudinal movement relative to the anvil frame between a closed position with the cartridge housing and the anvil surfaces in closely spaced relationship, and an open position with the cartridge housing and the anvil surfaces spaced farther from each other than in the closed position.

An elongate T-bar or "ram" is mounted in the ram channel between the first and second side portions for longitudinal movement relative to the cartridge transporting member and the anvil frame. The ram is adapted to engage and drive the pusher distally to fire the stapler when the cartridge housing the anvil surfaces are in the closed position.

An actuation means is present to initially move the cartridge assembly from the open to the closed position by a first movement of the lever part from the release to the actuation position and for subsequently firing the stapler (i.e. moving the ram distally relative to the cartridge transporting member to cause the pusher to eject the staples from the cartridge housing, to press the staples against the anvil surfaces and to engage and close the staples in tissue between the cartridge housing and the anvil jaw portion) by a second movement of the lever part from the release to the actuation position. Another biasing means biases the cartridge assembly from the closed to the open position. That biasing means preferably comprises a coil spring connected between the anvil frame and the ram.

The actuation means preferably comprises a toggle joint linkage having an over center pivoting portion and first and second ends with the first end fixed to the anvil frame and with the second end connected to the cartridge transporting member. The over center pivoting portion preferably has surfaces adapted to engage the lever part when the lever part is first moved from the release to the actuation positions to move the toggle joint linkage from a retracted position with the cartridge assembly in the open position past an in-line or centered position with the toggle joint linkage generally straight, to an extended position generally slightly inverted relative to the retracted position to drive the cartridge assembly from the open to the closed positions.

The actuation means also preferably includes means for retaining the cartridge assembly in the closed position against the bias of the coil spring that biases the cartridge assembly from the closed to the open position. Preferably, such a means comprises a stop flange on the over center pivoting portion of the toggle joint linkage that prevents the toggle joint linkage from moving beyond the extended position. Alternatively such a means may comprise a stop surface located on a handle cover.

The actuation means also preferably includes surfaces defining a cam shoulder surface on the ram, a pawl having first and second ends and a cam surface generally adjacent the second end of the pawl, and means mounting the pawl on the lever part for movement between a first position with the cam surface generally spaced from the cam shoulder surface on the ram and a second position with the cam surface engaged with the cam shoulder surface on the ram to afford firing of the stapler by driving the ram distally relative to the cartridge transporting member. Also preferably, the stapler includes means, such as a torsion spring, for biasing the pawl toward the second position, and the ram has surfaces which are adapted to retain the pawl in the first position until the cartridge assembly is moved from the open to the closed position.

Additionally, the stapler includes a release arm having a first end pivotally mounted to the proximal end of the anvil frame and a second engagement end. The release arm has surfaces adapted to engage the pawl and the toggle joint linkage to move the pawl from the second toward the first position and to move the toggle joint linkage from the extended toward the retracted position to afford movement of the cartridge assembly from the closed to the open position under the bias of the means for biasing the cartridge assembly from the closed to the open position (e.g. the coil spring).

Optionally, the stapler according to the present invention may include a means for preventing the cartridge assembly from moving from the open to the closed position when the stapler is loaded with a spent cartridge housing.

There is also present a safety guide member comprising (1) a sleeve slidably mounted on the anvil frame for longitudinal movement relative thereto and having proximal and distal ends, (2) an alignment pin assembly including a longitudinally extending alignment pin mounted on the distal end of the sleeve for movement between an alignment position with the pin passing through the cartridge housing alignment through passage and extending into the alignment aperture and a release position with the alignment pin spaced from the alignment through passage and the alignment aperture, and (3) means for preventing the cartridge assembly from moving from the open to the closed position unless the alignment pin is in the alignment position, and for preventing the alignment pin from moving from the alignment position toward the release position when the cartridge assembly is in the closed position.

The means for preventing the cartridge assembly from moving from the open to the closed position unless the alignment pin is in the alignment position, and for preventing the alignment pin from moving from the alignment position toward the release position when the cartridge assembly is in the closed position preferably comprises surfaces defining a safety notch in the anvil frame, cartridge transport member and ram, and a safety gate having cam shoulder surfaces and surfaces defining a hole. The surfaces defining a safety notch in the anvil frame, cartridge transport member and ram are aligned when the cartridge assembly is in the open position to define a continuous safety notch extending laterally across the stapler and are staggered when the cartridge assembly is in the closed position.

The safety gate is mounted adjacent the anvil frame for relative movement thereto between a latched position with the safety gate engaged with the surfaces defining the continuous safety notch to prevent relative movement between the cartridge assembly and the anvil frame, and an unlatched position with the safety gate spaced from the safety notches to afford relative movement of the cartridge assembly and the anvil frame between the open and closed positions.

The safety guide member includes safety gate deactivating guides projecting proximally from the proximal end of the sleeve and through the safety gate hole. The guides are adapted to bias the safety gate toward the latched position when the alignment pin is in a position other than the alignment position and have cam surfaces at a proximal end adapted to engage the cam shoulder surfaces of the safety gate to drive the safety gate from the latched to the unlatched position when the alignment pin is moved to the alignment position.

The means for preventing the alignment pin from moving from the alignment position toward the release position when the cartridge assembly is in the closed position includes the safety gate deactivating guides having return cam surfaces generally opposite the cam surfaces adapted to engage surfaces on the safety gate to drive the safety gate from the unlatched toward the latched position when the alignment pin is moved away from the alignment position, and surfaces on the cartridge transport member and ram adapted to engage the safety gate to prevent the return cam surfaces from driving the safety gate from the unlatched position toward the latched position to thereby prevent the alignment pin from moving from the alignment position toward the release position when the cartridge assembly is in the closed position.

BRIEF DESCRIPTION OF THE DRAWING

The present invention will be further described with reference to the accompanying drawing wherein like reference numerals refer to like parts in the several views, and wherein:

FIGS. 2 through 5 are enlarged first side views of the surgical instrument of FIG. 1 which sequentially illustrate the operation of the stapler wherein:

FIG. 2 shows the relative positions of the anvil frame and the cartridge assembly in an open position and has portions broken away to show details;

FIG. 3 illustrates the positions of the anvil frame and the cartridge assembly just after the cartridge assembly is moved to the closed position and has portions broken away to show details;

FIG. 4 shows the positions of the anvil frame and the cartridge assembly just before the stapler is fired and has portions broken away to show details;

FIG. 5 illustrates the stapler just after the stapler is fired;

FIG. 6 is an enlarged bottom view of the surgical instrument of FIG. 1 which has portions broken away to show details;

FIG. 7 is an enlarged sectional view of the stapler of FIG. 1 taken approximately along line 7—7 of FIG. 5;

FIG. 8 is an enlarged sectional view of the stapler of FIG. 1 taken approximately along line 8—8 of FIG. 2 and having portions broken away to show details;

FIG. 9 is an enlarged second side view of the stapler of FIG. 1 having portions broken away to show details of an actuation mechanism;

FIG. 10 is an enlarged second side view of the stapler of FIG. 1 having portions broken away to show details of an actuation mechanism and which illustrates the proximal end of the stapler;

FIG. 11 is an enlarged first side view of the stapler of FIG. 1 having portions broken away to show details of an actuation mechanism;

FIG. 12 is an enlarged first side view of the distal end of the stapler of FIG. 1 illustrating a pusher in a pre-fired position;

FIG. 13 is an enlarged first side view of the distal end of the stapler of FIG. 1 illustrating a pusher in a fired position;

FIG. 14 is an enlarged sectional view of the stapler of FIG. 13 taken approximately along line 14—14 of FIG. 13 and having portions broken away to show details;

DETAILED DESCRIPTION

Figure 1:
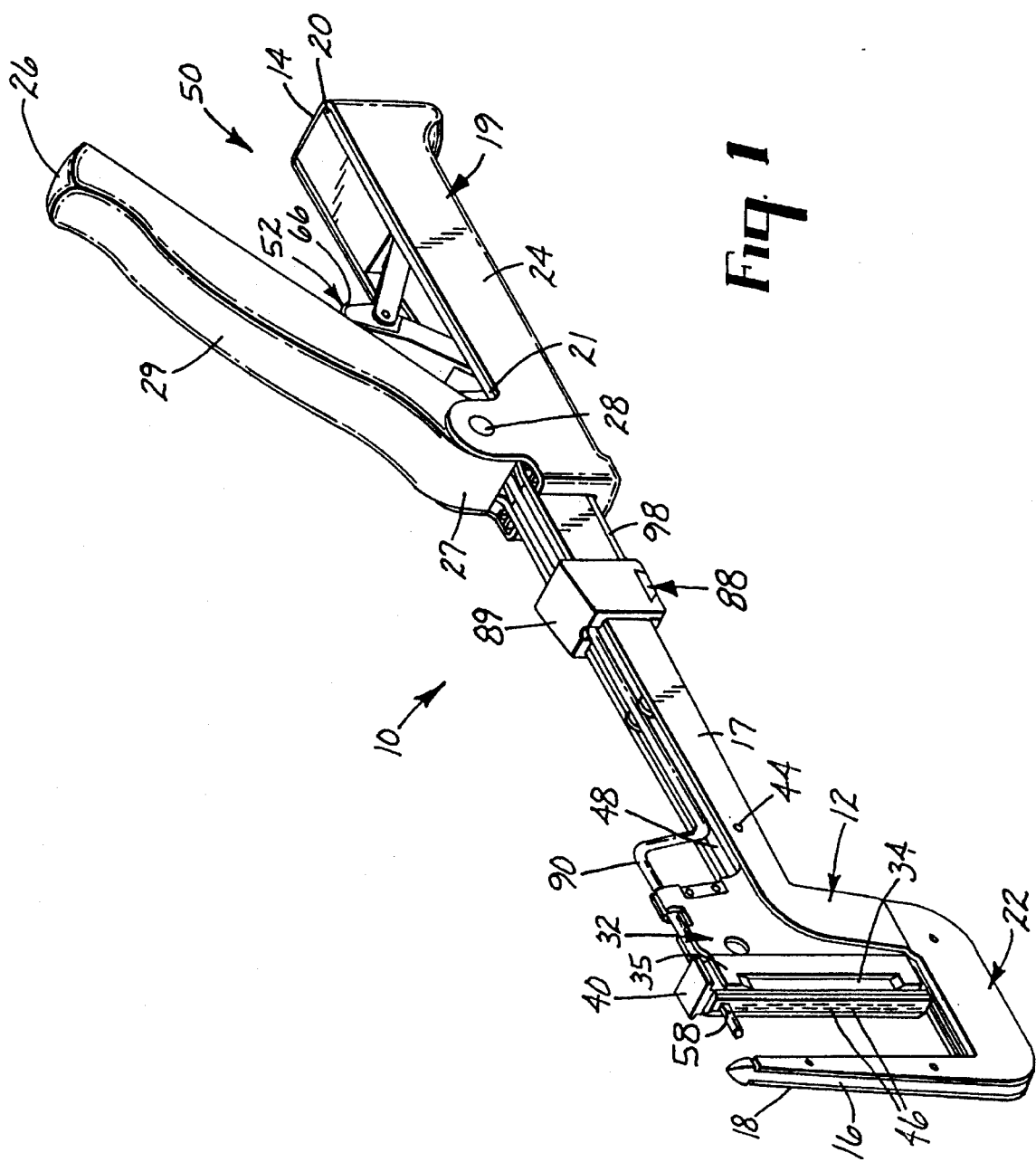
FIG. 1 is a perspective view of the surgical stapling instrument according to the present invention.
Figure 15:
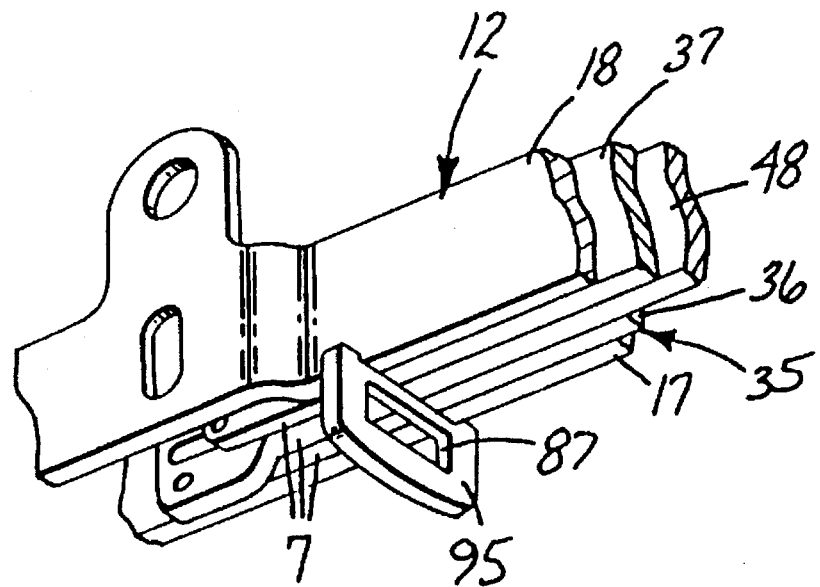
FIG. 15 is an enlarged perspective view of the stapler of FIG. 1 showing a safety gate in a latched position and having portions broken away to show detail.
Figure 16:
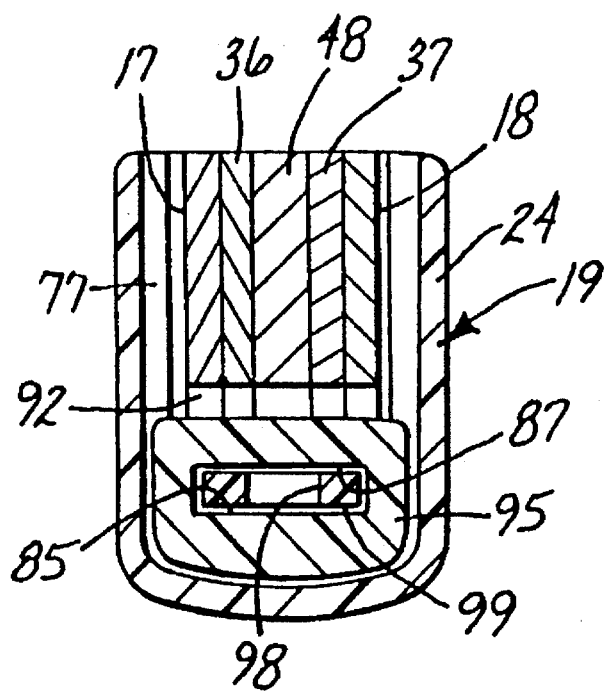
FIG. 16 is a sectional view of the stapler of FIG. 1 taken approximately along lines 16—16 of FIG. 9.

Referring now to FIGS. 1 through 16 of the drawing, there is shown a surgical stapling instrument according to the present invention, generally designated by the reference numeral 10.

Generally the surgical stapling instrument 10 comprises an anvil frame 12 having proximal 14 and distal 16 ends and a pair of lateral side portions 17 and 18 that are each elongate in a longitudinal direction and spaced to define a channel therebetween. The anvil frame 12 has a handle portion 19 generally adjacent the proximal end 14 with first 20 and second 21 ends, and a jaw portion 22 having anvil surfaces 23 generally adjacent the distal end 16. The anvil surfaces 23 are positioned in a plane generally perpendicular to the longitudinal direction. The jaw portion 22 includes surfaces defining an alignment aperture 15 opening onto the anvil surfaces 23, the function of which will be described later.

A handle housing 24 is attached to the anvil frame 12 and may be constructed from any suitable material such as but not limited to a polymeric material such as nylon, polypropylene, high density polyethylene, acrylonitrile butadiene styrene (ABS), polyetherimide, polystyrene, acetal or polycarbonate.

An elongate manually movable handle or lever part 25 (see FIG. 9) having first 26 and second 27 ends is pivotally mounted at its second end 27 to the anvil frame 12 by means such as a pin 28. A handle cover 29 is attached to the lever part 25 and may be constructed from any suitable material such as but not limited to a polymeric material similar to the material used to construct the handle housing 24. The handle cover 29 and the handle housing 24 are shaped to afford convenient, efficient manual grasping of the stapler 10 and may be snap fit to the lever part 25 and anvil frame 12 respectively.

The lever part 25 is connected to the anvil frame 12 at a position generally adjacent the second end 21 of the handle portion 19. The pin 28 mounts the handle part 25 and handle cover 29 to the anvil frame 12 to afford pivotal movement of the lever part 25 relative to the anvil frame 12 between a release position (FIGS. 1, 2 and 4) with the first end 26 of the lever part 25 being spaced from the first end 14 of the handle portion 19 and an actuation position (FIGS. 3 and 5) with the lever part 25 and the handle portion 19 in closely spaced relationship. A biasing means biases the lever part 25 toward the release position. Preferably the biasing means comprises an extension coil spring 30 mounted at one end to the anvil frame 12 and at the other end to the lever part 25.

A cartridge assembly 32 having proximal 33 and distal 34 ends is mounted in the channel between the lateral side portions 17 and 18 for longitudinal movement relative to the anvil frame 12. The cartridge assembly 32 comprises a cartridge transporting member 35 having first 36 and second 37 side portions that are each elongate in the longitudinal direction and that are spaced to define a ram channel therebetween. The first and second side portions 36 and 37 have surfaces defining a cartridge groove 38 generally adjacent the distal end 34 of the cartridge assembly 32. The cartridge groove surfaces 38 are adapted to releasably receive a cartridge housing 40.

The cartridge housing 40 includes a plurality of staples 41 disposed in rows oriented in planes generally perpendicular to the longitudinal direction and positioned in opposition to the anvil surfaces 23, and manually activatable means, such as a pusher 42, for pressing the staples 41 within longitudinal slots 46 in the cartridge housing 40 against specially shaped anvil surfaces 23 to engage and close the staples 41 in tissue between the cartridge housing 40 and the anvil surfaces 23. The pusher 42 has a pair of edges 43 and is positioned proximate the staples 41 for movement between pre-fired (FIG. 12) and fired (FIG. 13) positions with the pusher 42 adapted to move distally relative to the cartridge housing 40 when the stapler 10 is fired.

The cartridge housing 40 also has surfaces defining a close fitting hole or alignment through passage 58 positioned in opposition to the alignment aperture 15 in the anvil frame 12. The alignment through passage 58 and the alignment aperture 15 may be generally cylindrical and coaxial and perform a function to be described later.

Means such as pins 44 and grooves 45 mount the cartridge assembly 32 for longitudinal movement relative to the anvil frame 12 between a closed position (FIGS. 3, 4 and 5) with the cartridge housing 40 and the anvil surfaces 23 in closely spaced relationship, and an open position (FIGS. 1 and 2) with the cartridge housing 40 and the anvil surfaces 23 spaced farther from each other than in the closed position.

An elongate T-bar or ram 48 is mounted in the ram channel between the first and second side portions 36 and 37 of the cartridge transport member 35 for longitudinal movement relative to the cartridge transporting member 35 and the anvil frame 12. The T-bar or ram 48 is adapted to engage and drive the pusher 42 distally to eject the staples 41 from the cartridge housing 40 when the cartridge housing 40 and the anvil surfaces 23 are in the closed position.

FIGS. 2 through 5 sequentially illustrate the operation of the stapler 10. An actuation means 50 operable in a first movement of the lever part 25 from the release to the actuation position initially moves the cartridge assembly 32 from the open to the closed positions (FIG. 2 and 3). The actuation means 50 is operable in a second movement (FIGS. 4 and 5) of the lever part 25 from the release to the actuation position to subsequently fire the stapler 10 (e.g. the actuation means 50 drives the ram 48 distally relative to the cartridge transporting member 35 to move the pusher 42 distally to eject the staples 41 from the cartridge housing 40 to press the staples 41 against the anvil surfaces 23 and to engage and close the staples 41 in tissues between the cartridge housing 40 and the anvil jaw portion 22). A means such as a coil spring 51 connected between the anvil frame 12 and the ram 48 biases the cartridge assembly 32 from the closed to the open position and is overcome by the actuation means 50.

The actuation means 50 preferably comprises a toggle joint linkage 52 having an over center pivoting portion 53 and first 54 and second 55 ends with the first end 54 pivotally mounted to the anvil frame 12 by pin 56 and with the second end 55 pivotally connected to the cartridge transporting member 35 by a pin 57. The over center pivoting portion 53 preferably has surfaces adapted to engage cooperable surfaces on the lever part 25 when the lever part 25 is first moved from the release to the actuation positions to move the toggle joint linkage 52 from a retracted position (FIGS. 1 and 2) with the cartridge assembly 32 in the open position past an in-line or centered position with the toggle joint linkage generally straight, to an extended position (FIGS. 3, 4, 5 and 10) with the toggle joint linkage 52 generally slightly inverted relative to the retracted position to drive the cartridge assembly 32 from the open to the closed positions.

The actuation means also preferably includes means for retaining the cartridge assembly 32 in the closed position against the bias of the coil spring 51 for biasing the cartridge assembly 32 from the closed to the open position. Preferably, such a means comprises a stop flange 66 on the over center pivoting portion 53 of the toggle joint linkage 52. The stop flange 66 is adapted to engage surfaces on the toggle joint linkage 52 to prevent the toggle joint linkage 52 from moving past the extended position. Alternatively such a means may comprise a stop surface located on the handle housing 24. Also, a relatively weak torsion spring (not shown) may be mounted on the over center pivoting portion 53 of the toggle joint linkage 52 to bias the toggle joint linkage 52 toward the extended position and to prevent the cartridge assembly from accidentally opening when the lever part 25 is moved from the actuation to the release position just after firing the stapler 10.

Additionally, the actuation means 50 preferably includes surfaces defining a cam shoulder surface 49 on the ram 48, and a pawl 60 having first 61 and second 62 ends and a cam surface 63 generally adjacent the second end 62. A means such as pin 64 mounts the pawl 60 on the lever part 25 for movement between a first position (FIGS. 2, 3 and 9) with the cam surface 63 spaced from the cam shoulder surface 49 on the ram 48 and a second position (FIGS. 4, 10 and 11) with the cam surface 63 engaged with the cam shoulder surface 49 on the ram 48 to afford firing of the stapler 10 by driving the ram 48 distally relative to the cartridge transporting member 35 when the lever part 25 is moved from the release to the actuation position a second time. Also preferably, the stapler 10 further includes means for biasing the pawl toward the second position such as torsion spring 65, and the ram 48 has sliding surfaces 47 adapted to retain the pawl 60 in the first position until the cartridge assembly 32 is moved from the open to the closed position.

Additionally, the stapler 10 preferably further includes a release arm 70 having a first end pivotally mounted to the proximal end 14 of the anvil frame 12 by pin 56 and a second end connected to manually activatable release button 72 extending laterally from the handle housing 24. The release arm 70 has surfaces 73 adapted to engage shoulder portions or pin 67 of the pawl 60 and laterally inwardly projecting surfaces (not shown) adapted to engage the over center portion 53 of the toggle joint linkage 52 to initially move the pawl 60 from the second toward the first position and to then move the toggle joint linkage 52 from the extended toward the retracted position to afford movement of the cartridge assembly 32 from the closed to the open position under the bias of spring 51.

The function of the alignment through passage 58 and the alignment aperture 15 will now be described relative to the function of a safety guide member 88 comprising a sleeve 89 having proximal and distal ends. The sleeve 89 is slidably mounted on the anvil frame 12 for longitudinal movement relative thereto. A longitudinally extending alignment or retention pin 90 is mounted on the distal end of the sleeve 89 for movement between an alignment position (FIGS. 3, 4 and 5) with the alignment pin 90 passing through the cartridge housing alignment through passage 58 and extending into the alignment aperture 15 and a release position (FIGS. 1 and 2) with the alignment pin 90 spaced from the alignment through passage 58 and the alignment aperture 15 to afford removal and replacement of the cartridge housing with a new cartridge housing. In the alignment position, the alignment pin 90 is adapted to position the rows of staples 41 relative to the specially shaped surfaces 23 on the anvil frame 12 to afford a more precisely controlled formation of fired staples and to prevent tissue from escaping from between the cartridge housing 40 and the anvil surfaces 23 when the cartridge assembly 32 is moved to the closed position.

There is also present means 94 for preventing the cartridge assembly 32 from moving from the open to the closed position unless the alignment pin 90 is in the alignment position, and for preventing the alignment pin 90 from moving from the alignment position toward the release position when the cartridge assembly 32 is in the closed position comprising surfaces defining a safety notch 92 in the cartridge assembly 32 (including both the ram 48 and the cartridge transport member 35) and the anvil frame 12.

The surfaces defining a safety notch 92 in the anvil frame 12, cartridge transport member 35 and ram 48 are aligned when the cartridge assembly 32 is in the open position to define a continuous safety notch (FIGS. 2, 9, 15 and 16) extending laterally across the stapler 10 and are staggered (see FIGS. 3, 4 and 10) when the cartridge assembly 32 is in the closed position.

The means 94 includes a safety gate 95 (FIGS. 15 and 16) having cam shoulder surfaces 85 and return cam surfaces 8 generally opposite the cam surfaces 85. The safety gate 95 includes surfaces defining a safety gate hole 87. The safety gate 95 is mounted adjacent the anvil frame 12 for relative movement thereto between a latched position (FIG. 2) with the safety gate 95 engaged with the surfaces defining the continuous safety notch 92 to prevent relative movement between the cartridge assembly 32 and the anvil frame 12 when the cartridge assembly 32 is in the open position, and an unlatched position (FIGS. 3, 4 and 9) with the safety gate 95 spaced from the safety notch 92 to afford relative longitudinal movement of the cartridge assembly 32 and the anvil frame 12 between the open and closed positions. The handle housing 24 includes guide surfaces defining a slot 77 that affords reciprocating movement of the safety gate 95 between the latched and unlatched positions.

As part of the means 94, the safety guide member 88 includes safety gate deactivating guides 98 projecting proximally from the proximal end of the sleeve 89 and through the safety gate hole 87. Return cam surfaces 8 of the guides 98 bias the safety gate 95 toward the latched position when the alignment pin 90 is in a position other than the alignment position. The cam surfaces 99 at a proximal end of the guides 98 are adapted to engage the cam shoulder surfaces 85 of the safety gate 95 to drive the safety gate 95 from the latched to the unlatched position when the alignment pin 90 is moved to the alignment position. Surfaces 7 (FIG. 15) on the cartridge transport member 35 and ram 48 are adapted to engage the "top" of the safety gate 95 to prevent the return cam surfaces 8 from driving the safety gate 95 from the unlatched position toward the latched position when the cartridge assembly is in the closed position. Thus, once the alignment pin 90 is moved to the aligned position, the means 94 also prevents the alignment pin 90 from moving from the alignment position toward the release position when the cartridge assembly 32 is in the closed position.

The stapler 10 may optionally include a means preventing the cartridge assembly from moving from the open to the closed position unless the stapler 10 is loaded with a ready-to-fire staple cartridge.

As best seen in FIGS. 12 though 14, the stapler 10 may comprise a means for preventing the cartridge assembly 32 from moving from the open to the closed position when the stapler 10 is loaded with a cartridge housing 40 having means for pressing the staples 41 within the cartridge housing 40 against the anvil surfaces (e.g. a pusher 42) in a fired position. Such a means prevents approximation and clamping of living tissue between anvil (e.g. 23) and cartridge (e.g. 40) components of the stapler 10 when the stapler 10 is loaded with a spent stapler cartridge, and prevents firing of the stapler 10 when the stapler is loaded with a spent stapler cartridge.

FIGS. 12 through 14 illustrate a stapler 10 wherein the means for preventing the cartridge assembly 32 from moving from the open to the closed position comprises the anvil frame 12 having surfaces defining a safety aperture 81 opening into the surface of the anvil frame 12 and having a bottom surface, and a locking pin 82 having first 83 and second 84 ends. The locking pin 82 is mounted within the safety aperture 81 for movement between a free travel position (FIG. 12) with the first end 83 of the locking pin 82 generally abutting an edge 43 of the pusher 42 to afford a single, reciprocating movement of the cartridge assembly 32 between the open and closed positions, and a blocking position (FIG. 13) with the first end 83 of the locking pin 82 projecting beyond the safety aperture 81 and into the path of the ram 48 to prevent movement of the cartridge assembly 32 from the open to the closed position. A biasing means (such as a coil spring 86 having a first end connected to the second end 84 of the locking pin 82 and a second end connected to the bottom surface of the safety aperture 81) biases the locking pin 82 toward the blocking position.

OPERATION

The operation of the present invention may now be described with reference to the stapler 10. FIGS. 2 through 5 sequentially illustrate the operation of the stapler 10.

FIG. 2 illustrates the relative positions of the anvil frame 12 and the cartridge assembly 32 in an open position. Typically the stapler 10 may be positioned adjacent the tissue to be stapled, and the alignment pin 90 is then moved from the release position (FIG. 2) to the alignment position (FIGS. 3, 4 and 5) by moving the sleeve 89 distally. When the alignment pin 90 is located in the alignment position, the cam surfaces 99 move the safety gate 95 to the unlatched position to afford relative movement between the cartridge assembly 32 and the anvil frame 12.

In the alignment position, the alignment pin 90 passes through the cartridge housing alignment through passage 58 and extends into the alignment aperture 15 to orient and position the rows of staples 41 relative to the specially shaped surfaces 23 on the anvil frame 12 to afford a more precisely controlled formation of fired staples. Placing the alignment pin 90 in the alignment position also prevents tissue from escaping from between the cartridge housing 40 and the anvil surfaces 23 when the cartridge assembly 32 is moved to the closed position.

FIG. 3 illustrates the positions of the anvil frame 12 and the cartridge assembly 32 just after the cartridge assembly 32 is moved to the closed position by a first movement of the lever part 25 from the release position to the actuation position, after which the coil spring 30 returns the lever part 25 to the release position shown in FIG. 4. When the cartridge assembly is in the closed position, the surfaces 7 (FIG. 15) on the cartridge transport member 35 and ram 48 are adapted to engage the "top" of the safety gate 95 and prevent the return cam surfaces 8 from driving the safety gate 95 from the unlatched position toward the latched position. Thus, once the alignment pin 90 is moved to the aligned position as shown in FIG. 3, the means 94 also prevents the alignment pin 90 from moving from the alignment position toward the release position when the cartridge assembly 32 is in the closed position. This feature prevents a user from (1) clamping the stapler 10 on the tissue to be stapled and (2) thereafter moving the alignment pin 90 from the alignment position.

FIG. 4 shows the positions of the anvil frame 12 and the cartridge assembly 32 just before the stapler 10 is fired. After the cartridge assembly 32 is moved to the closed position, the pawl 60 moves to the second position with the cam surface 63 generally engaged with the cam shoulder surface 49 of the ram 48. In this position, the stapler 10 is ready to be fired. A second movement of the lever part 25 from the release position to the actuation position (FIG. 5) causes the ram 48 to move distally relative to the cartridge transport member 35 and the anvil frame 12, which drives the pusher 42 distally to eject the staples 41 from the cartridge housing 40 to press the staples 41 against the specially shaped anvil surfaces 23 and to engage and close the staples 41 in tissues between the cartridge housing 40 and the anvil jaw portion 22.

Once the cartridge assembly 32 is moved to the closed position, the spring 51 biases the cartridge assembly toward the open position but is prevented from moving the cartridge assembly 32 to the open position by engagement between a stop flange 66 of the toggle joint linkage 52 with another portion of the toggle joint linkage 52 generally adjacent the over center pivoting portion 53. Optionally, engagement between the toggle joint linkage 52 and surfaces on the handle housing 24 may prevent further downward movement of the toggle joint linkage 52. A torsion spring (not shown) prevents the toggle joint linkage from accidentally "popping-up" or returning to the retracted position when the stapler 10 is fired.

After the stapler 10 is fired, the user may control the return of the cartridge assembly 32 to the open position by moving manually activatable release button 72 "upward" to engage surfaces 73 of release arm 70 with shoulder portions or pin 67 of the pawl 60 and to engage laterally inwardly projecting surfaces (not shown) on the arm 70 with the over center portion 53 of the toggle joint linkage 52 to move the pawl 60 from the second toward the first position and to move the toggle joint linkage 52 from the extended toward the retracted position against the bias of the torsion spring (not shown). Such a movement of the release arm 70 allows the spring 51 to return the cartridge assembly 32 to the open position.

Once the cartridge assembly 32 is moved to the open position, the return cam surfaces 8 are free to drive the safety gate 95 into engagement with the safety notch 92 to prevent the cartridge assembly 32 from moving from the open to the closed position unless the alignment pin 90 is again moved to the alignment position. Thus, the safety mechanism of the present invention operates continuously, even if the stapler is subsequently reused, for example, in the same patient.

As best seen in FIG. 13, after the stapler 10 is fired and the cartridge assembly 32 is moved to the open position, the pusher 42 is located closer to the cartridge housing 40 than in the pre-fired position so that the second end of pin 82 no longer engages the edge 43 of pusher 42. Thus after the ram 48 moves back to the open position, the spring 86 biases the pin 82 from the free-travel to the blocking position with the first end 83 of the locking pin 82 projecting beyond the safety aperture 81 and into the path of the ram 48 to thereby prevent movement of the cartridge assembly 32 from the open to the closed position. It should be pointed out that the pin 82 will not only prevent the stapler 10 from firing when loaded with a spent cartridge, but will also prevent the firing of the stapler 10 when the stapler is not loaded with a cartridge housing 40 at all.

Also, the pin 82 prevents firing of the stapler 10 should the fired cartridge housing be replaced with another fired cartridge, since the edge portion of the pusher of the fired cartridge would not be able to move the pin 82 from the blocking to the free-travel position. The stapler 10 can be refired only by replacing the fired cartridge housing with an unfired or ready-to-fire cartridge housing 40 having an edge surface 43 of the pusher 42 in the proper position to move the pin 82 to the free-travel position.

It should be noted that the mechanical advantage provided by the toggle joint linkage 52 is at its minimum when the cartridge assembly 32 is in the open position and generally increases as the cartridge assembly 32 moves toward the closed position. Thus, it is important to prevent the cartridge assembly 32 from moving from the open toward the closed position to thereby minimize the shear force transmitted through the toggle joint linkage 52 to the pin 82.

The present invention has now been described with reference to several embodiments thereof. It will be apparent to those skilled in the art that many changes can be made in the embodiment described without departing from the scope of the present invention. For example, the anvil frame 12 and cartridge assembly 32 may be constructed from any suitable material, such as, but not limited to metal or plastic. Thus the scope of the present invention should not be limited to the structure described in this application, but only by structures described by the language of the claims and the equivalents of those structures.

What is claimed is:

1. A surgical stapler comprising:

an anvil frame having proximal and distal ends and a pair of lateral side portions each being elongate in a longitudinal direction and spaced to define a channel therebetween, said anvil frame having a handle portion generally adjacent said proximal end and having first and second ends, and a jaw portion having specially shaped anvil surfaces generally adjacent said distal end and positioned in a plane generally perpendicular to said longitudinal direction, said jaw portion including surfaces defining an alignment aperture opening onto said anvil surfaces, an elongate manually movable handle part having first and second ends, said handle part having pivot means at said second end adapted for affording relative pivotal movement of said handle part and said anvil frame between a release position with said first end of said handle part being spaced from said first end of said handle portion and an actuation position with said handle part and said handle portion in closely spaced relationship;

biasing means for biasing said handle portion toward said release position, a cartridge assembly having proximal and distal ends and being mounted in said channel between said lateral side portions for longitudinal movement relative to said anvil frame;

said cartridge assembly comprising: a cartridge transporting member having first and second side portions each being elongate in said longitudinal direction and being spaced to define a ram channel therebetween, said first and second side portions having surfaces defining a cartridge groove generally adjacent said distal end of said cartridge assembly, said cartridge groove surfaces being adapted to releasably receive a cartridge housing containing a plurality of staples disposed in rows positioned in opposition to said anvil surfaces, the cartridge housing having surfaces defining an alignment through passage positioned in opposition to the alignment aperture, means for mounting said cartridge assembly for longitudinal movement relative to said anvil frame between a closed position with said cartridge housing and said anvil surfaces in closely spaced relationship, and an open position with said cartridge housing and said anvil surfaces spaced farther from each other than in said closed position, an elongate ram being mounted in said ram channel between said first and second side portions for longitudinal movement relative to said cartridge transporting member and said anvil frame, said ram being adapted for ejecting the staples from the cartridge housing to press the staples against said anvil surfaces and to engage and close the staples in tissues between said cartridge housing and said anvil jaw portion when said cartridge housing and said anvil surfaces are in said closed position, actuation means operable in a first movement of said handle part from said release to said actuation positions to initially move said cartridge assembly from said open to said closed positions and operable in a second movement of said handle part from said release to said actuation positions to subsequently fire said stapler by moving said ram distally relative to said cartridge transporting member to eject the staples from the cartridge housing to press the staples against said anvil surfaces and to engage and close the staples in tissues between said cartridge housing and said anvil jaw portion, means for biasing said cartridge assembly from said closed to said open position, and a safety guide member comprising:

a sleeve having proximal and distal ends and being slidably mounted on said anvil frame for longitudinal movement relative thereto, a longitudinally extending alignment pin mounted on said distal end of said sleeve for movement between an alignment position with said pin passing through said cartridge housing alignment through passage and extending into said alignment aperture to position said rows of staples relative to said specially shaped surfaces on said anvil to afford a more precisely controlled formation of fired staples and to prevent tissue from escaping from between the cartridge housing and the anvil surfaces when the cartridge assembly is moved to the closed position, and a release position with said alignment pin spaced from said alignment through passage and said alignment aperture to afford removal and replacement of said cartridge housing with a new cartridge housing, and means, mounted on said safety guide member, for repeatably and continuously preventing said cartridge assembly from moving from said open to said closed position unless said alignment pin is in said alignment position.

2. A surgical stapler comprising:

an anvil frame having proximal and distal ends and a pair of lateral side portions each being elongate in a first longitudinal direction and spaced to define a channel therebetween, said anvil frame having a handle portion generally adjacent said proximal end and having first and second ends, and a jaw portion having specially shaped anvil surfaces generally adjacent said distal end and positioned in a plane generally perpendicular to said first longitudinal direction, said jaw portion including surfaces defining an alignment aperture opening onto said anvil surfaces, an elongate manually movable handle part having first and second ends, said handle part having pivot means at said second end adapted for affording relative pivotal movement of said handle part and said anvil frame between a release position with said first end of said handle part being spaced from said first end of said handle portion and an actuation position with said handle part and said handle portion in closely spaced relationship;

biasing means for biasing said handle portion toward said release position, a cartridge assembly having proximal and distal ends and being mounted in said channel between said lateral side portions for longitudinal movement relative to said anvil frame;

said cartridge assembly comprising: a cartridge transporting member having first and second side portions each being elongate in said longitudinal direction and being spaced to define a ram channel therebetween, said first and second side portions having surfaces defining a cartridge groove generally adjacent said distal end of said cartridge assembly, said cartridge groove surfaces being adapted to releasably receive a cartridge housing containing a plurality of staples disposed in rows positioned in opposition to said anvil surfaces, the cartridge housing having surfaces defining an alignment through passage positioned in opposition to the alignment aperture, and means mounting said cartridge assembly for longitudinal movement relative to said anvil frame between a closed position with said cartridge housing and said anvil surfaces in closely spaced relationship, and an open position with said cartridge housing and said anvil surfaces spaced farther from each other than in said closed position, an elongate ram being mounted in said ram channel between said first and second side portions for longitudinal movement relative to said cartridge transporting member and said anvil frame, said ram being adapted for ejecting the staples from the cartridge housing to press the staples against said anvil surfaces and to engage and close the staples in tissues between said cartridge housing and said anvil jaw portion when said cartridge housing and said anvil surfaces are in said closed position, actuation means operable in a first movement of said handle part from said release to said actuation positions to initially move said cartridge assembly from said open to said closed positions and operable in a second movement of said handle part from said release to said actuation positions to subsequently fire said stapler by moving said ram distally relative to said cartridge transporting member to eject the staples from the cartridge housing to press the staples against said anvil surfaces and to engage and close the staples in tissues between said cartridge housing and said anvil jaw portion, means for biasing said cartridge assembly from said closed to said open position, and a safety guide member comprising: a sleeve having proximal and distal ends and being slidably mounted on said anvil frame for longitudinal movement relative thereto, a longitudinally extending alignment pin mounted on said distal end of said sleeve for movement between an alignment position with said pin passing through said cartridge housing alignment through passage and extending into said alignment aperture to position said rows of staples relative to said specially shaped surfaces on said anvil to afford a more precisely controlled formation of fired staples and to prevent tissue from escaping from between the cartridge housing and the anvil surfaces when the cartridge assembly is moved to the closed position, and a release position with said alignment pin spaced from said alignment through passage and said alignment aperture to afford removal and replacement of said cartridge housing with a new cartridge housing, and means for repeatably and continuously preventing said cartridge assembly from moving from said open to said closed position unless said alignment pin is in said alignment position comprising:

said anvil frame, cartridge transport member and ram each having surfaces defining safety notches which are aligned when said cartridge assembly is in said open position, a safety gate having cam shoulder surfaces and surfaces defining a hole, said safety gate being mounted adjacent said anvil frame for relative movement thereto between a latched position with the safety gate engaged with the surfaces defining the safety notches to prevent relative movement between the cartridge assembly and the anvil frame when the cartridge assembly is in said open position, and an unlatched position with the safety gate spaced from said safety notches to afford relative movement of the cartridge assembly and the anvil frame between the open and closed positions, and said safety guide member including safety gate deactivating guides projecting proximally from the proximal end of said sleeve and through said safety gate hole, said guides being adapted to drive said safety gate toward said latched position when the alignment pin is in a position other than the alignment position and having cam surfaces at a proximal end adapted to engage the cam shoulder surfaces of said safety gate to drive the safety gate from said latched to said unlatched position when the alignment pin is moved to the alignment position.

3. A stapler according to claim 2 wherein said stapler includes means for preventing said alignment pin from moving from said alignment position toward said release position when said cartridge assembly is in said closed position comprising:

said safety gate deactivating guides having return cam surfaces generally opposite said cam surfaces adapted to engage surfaces on said safety gate to drive the safety gate from the unlatched toward the latched position when the alignment pin is moved away from the alignment position, and surfaces on said cartridge transport member and ram adapted to engage the safety gate to prevent the alignment pin from moving from the alignment position toward the release position when the cartridge assembly is in the closed position.

4. A stapler comprising:

an elongate anvil including anvil surfaces in a plane generally perpendicular to the direction of elongation of said anvil, and surfaces defining an alignment aperture opening onto said anvil surfaces, a cartridge assembly movable relative to said anvil between an open position with the cartridge assembly spaced from said anvil surfaces and a closed position with said cartridge assembly and said anvil surfaces in closely spaced relationship, a longitudinally extending alignment pin mounted on said stapler for movement between an alignment position with said alignment pin extending into said alignment aperture, and a release position with said alignment pin spaced from said alignment aperture, and means adapted to engage said cartridge assembly for repeatedly and continuously preventing said cartridge assembly from moving from said open toward said closed position whenever said alignment pin is in a position other than said alignment position comprising:

surfaces defining a safety notch in said cartridge assembly and anvil when said cartridge assembly is in said open position, a safety gate having cam shoulder surfaces and surfaces defining a hole, said safety gate being mounted adjacent said anvil for relative movement thereto between a latched position with the safety gate engaged with the surfaces defining the safety notch to prevent relative movement between the cartridge assembly and the anvil, and an unlatched position with the safety gate spaced from said safety notch to afford relative movement of the cartridge assembly and the anvil between the open and closed positions, and a safety guide member including a sleeve with safety gate deactivating guides projecting proximally from a proximal end of said sleeve and through said safety gate hole, said guides being adapted to bias said safety gate toward said latched position when the alignment pin is in a position other than the alignment position and having cam surfaces at a proximal end adapted to engage the cam shoulder surfaces of said safety gate to drive the safety gate from said latched to said unlatched position when the alignment pin is moved to the alignment position.

5. A stapler according to claim 4 wherein said cartridge assembly includes a cartridge transport member, said stapler includes a ram, and said stapler includes means for preventing said alignment pin from moving from said alignment position toward said release position when said cartridge assembly is in said closed position comprising:

said safety gate deactivating guides having return cam surfaces generally opposite said cam surfaces, said return cam surfaces being adapted to engage surfaces on said safety gate to drive the safety gate from the unlatched toward the latched position when the alignment pin is moved away from the alignment position, and surfaces on said cartridge transport member and ram adapted to engage the safety gate to prevent the return camming surfaces from driving the safety gate to the latched position to thereby prevent the alignment pin from moving from the alignment position toward the release position when the cartridge assembly is in the closed position.

6. A surgical stapler comprising:

an anvil elongate in a longitudinal direction and including anvil surfaces and surfaces defining an alignment aperture opening onto said anvil surfaces, a cartridge assembly movable relative to said anvil between an open position with the cartridge assembly spaced from said anvil surfaces and a closed position with said cartridge assembly and said anvil surfaces in closely spaced relationship, a longitudinally extending alignment pin mounted on said stapler for movement between an alignment position with said alignment pin extending into said alignment aperture, and a release position with said alignment pin spaced from said alignment aperture, and means adapted to engage said cartridge assembly for continuously, repeatedly and automatically preventing said cartridge assembly from moving from said open to said closed position whenever said alignment pin is in a position other than said alignment position, and for preventing said alignment pin from moving from said alignment position toward said release position when said cartridge assembly is in said closed position even after said cartridge assembly has been initially moved from said open position to said closed position and then returned to said open position.

7. A surgical stapler comprising:

an anvil elongate in a longitudinal direction and including anvil surfaces in a plane generally perpendicular to said longitudinal direction and surfaces defining an alignment aperture opening onto said anvil surfaces, a cartridge assembly movable relative to said anvil between an open position with the cartridge assembly spaced from said anvil surfaces and a closed position with said cartridge assembly and said anvil surfaces in closely spaced relationship, a longitudinally extending alignment pin mounted on said stapler for movement between an alignment position with said alignment pin extending into said alignment aperture, and a release position with said alignment pin spaced from said alignment aperture, and means for continuously preventing said cartridge assembly from moving from said open to said closed position whenever said alignment pin is in a position other than said alignment position, and for preventing said alignment pin from moving from said alignment position toward said release position when said cartridge assembly is in said closed position even after said cartridge assembly has been initially moved from said open position to said closed position and then returned to said open position.

8. A stapler according to claim 7 wherein said means for continuously preventing said cartridge assembly from moving from said open to said closed position whenever said alignment pin is in a position other than said alignment position, and for preventing said alignment pin from moving from said alignment position toward said release position when said cartridge assembly is in said closed position comprises:

a safety guide member comprising:

a sleeve having proximal and distal ends and being slidably mounted on said anvil for longitudinal movement relative thereto, said anvil and cartridge assembly each having surfaces defining safety notches which are aligned when said cartridge assembly is in said open position and which are staggered when said cartridge assembly is in said closed position, a safety gate having cam shoulder surfaces and surfaces defining a hole, said safety gate being mounted adjacent said anvil for relative movement thereto between a latched position with the safety gate engaged with the surfaces defining the safety notches to prevent relative movement between the cartridge assembly and the anvil when the cartridge assembly is in said open position, and an unlatched position with the safety gate spaced from said safety notches to afford relative movement of the cartridge assembly and the anvil between the open and closed positions, said safety guide member including safety gate deactivating guides projecting proximally from the proximal end of said sleeve and through said safety gate hole, said guides having return cam surfaces to bias said safety gate toward said latched position when the alignment pin is in a position other than the alignment position and having cam surfaces generally opposite said return cam surfaces that are adapted to engage the cam shoulder surfaces of said safety gate to drive the safety gate from said latched to said unlatched position when the alignment pin is moved to the alignment position, and surfaces on said cartridge assembly adapted to engage the safety gate to prevent the alignment pin from moving from the alignment position toward the release position when the cartridge assembly is in the closed position.

9. A surgical stapler comprising:

an elongate anvil including anvil surfaces, a cartridge assembly movable relative to said anvil between an open position with the cartridge assembly spaced from said anvil surfaces and a closed position with said cartridge assembly and said anvil surfaces in closely spaced relationship, an alignment pin assembly including an alignment pin, said alignment pin being mounted on said stapler for movement between an alignment position adapted to align the cartridge assembly with said anvil surfaces and a release position with said alignment pin spaced from said anvil surfaces, barrier means., mounted on said alignment pin assembly, for continuously and automatically preventing said cartridge assembly from moving from said open toward said closed position whenever said alignment pin is in a position other than said alignment position such that, once said alignment pin has been initially moved from said release toward said alignment position, said barrier means thereafter prevents said cartridge assembly from moving from said open toward said closed position, surfaces defining a safety notch in said cartridge assembly and anvil when said cartridge assembly is in said open position, and said barrier means comprises:

a safety gate having cam shoulder surfaces and surfaces defining a hole, said safety gate being mounted on said alignment pin assembly for relative movement thereto between a latched position with the safety gate engaged with the surfaces defining the safety notch to prevent relative movement between the cartridge assembly and the anvil, and an unlatched position with the safety gate spaced from said safety notch to afford relative movement of the cartridge assembly and the anvil between the open and closed positions.

10. A surgical stapler according to claim 9 wherein said alignment pin assembly comprises a safety guide member including a sleeve with safety gate deactivating guides projecting proximally from a proximal end of said sleeve and through said safety gate hole, said guides being adapted to bias said safety gate toward said latched position when the alignment pin is in a position other than the alignment position and having cam surfaces at a proximal end adapted to engage the cam shoulder surfaces of said safety gate to drive the safety gate from said latched toward said unlatched position when the alignment pin is moved toward the alignment position.

11. A stapler according to claim 10 wherein said cartridge assembly includes a cartridge transport member, said stapler includes a ram, and said stapler includes means for preventing said alignment pin from moving from said alignment position toward said release position when said cartridge assembly is in said closed position comprising:

said safety gate deactivating guides having return cam surfaces generally opposite said cam surfaces, said return cam surfaces being adapted to engage surfaces on said safety gate to drive the safety gate from the unlatched toward the latched position when the alignment pin is moved away from the alignment position, and surfaces on said cartridge transport member and ram adapted to engage the safety gate to prevent the return cam surfaces from driving the safety gate toward the latched position to thereby prevent the alignment pin from moving from the alignment position toward the release position when the cartridge assembly is in the closed position.

* * * * *